United States Patent
Asselin et al.

(10) Patent No.: US 8,781,275 B2
(45) Date of Patent: Jul. 15, 2014

(54) LASER ASSEMBLY WITH SHOCK ABSORBER

(75) Inventors: William Asselin, Lunenburg, MA (US); Jessica Hixon, Worcester, MA (US); Michael O'Brien, Boston, MA (US); Michael Melanson, Worcester, MA (US); Ty Fairneny, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 129 days.

(21) Appl. No.: 13/186,268

(22) Filed: Jul. 19, 2011

(65) Prior Publication Data
US 2012/0027351 A1 Feb. 2, 2012

Related U.S. Application Data
(60) Provisional application No. 61/368,130, filed on Jul. 27, 2010.

(51) Int. Cl.
G02B 6/26 (2006.01)
A61B 18/22 (2006.01)

(52) U.S. Cl.
USPC .............................................. 385/39; 606/15

(58) Field of Classification Search
USPC .................................................... 606/16, 17
See application file for complete search history.

(56) References Cited

U.S. PATENT DOCUMENTS

| | | | |
|---|---|---|---|
| 4,295,289 A | | 10/1981 | Snyder |
| 4,718,746 A | * | 1/1988 | Chrepta ........................... 385/74 |
| 4,740,047 A | | 4/1988 | Abe et al. |
| 4,861,804 A | * | 8/1989 | Nakanishi ........................ 521/54 |
| 4,884,862 A | * | 12/1989 | Kofod ............................. 385/55 |
| 5,242,437 A | | 9/1993 | Everett et al. |
| 5,246,436 A | | 9/1993 | Rowe |
| 5,428,699 A | | 6/1995 | Pon |
| 5,499,314 A | * | 3/1996 | Leite et al. ..................... 385/135 |
| 5,638,483 A | | 6/1997 | Konwitz |
| 5,944,389 A | * | 8/1999 | Zenba et al. ............. 297/452.48 |
| 5,946,441 A | | 8/1999 | Esch |
| 6,143,018 A | | 11/2000 | Beuthan et al. |
| 6,361,530 B1 | | 3/2002 | Mersch |
| 6,576,163 B2 | | 6/2003 | Mersch |
| 7,627,208 B2 | * | 12/2009 | Kuroiwa ......................... 385/31 |
| 2003/0199860 A1 | | 10/2003 | Loeb et al. |
| 2007/0106286 A1 | | 5/2007 | Harschack et al. |
| 2009/0287199 A1 | | 11/2009 | Hanley et al. |
| 2009/0287200 A1 | | 11/2009 | Hanley et al. |

(Continued)

FOREIGN PATENT DOCUMENTS

| | | |
|---|---|---|
| DE | 27 08 014 A1 | 8/1978 |
| JP | 59069702 A * | 4/1984 |

OTHER PUBLICATIONS

Partial International Search Report issued in International Application No. PCT/US2011/044951, mailed Nov. 2, 2011.

(Continued)

*Primary Examiner* — Omar Rojas

(74) *Attorney, Agent, or Firm* — Bookoff McAndrews, PLLC

(57) ABSTRACT

Embodiments of the invention include an apparatus including an optical fiber having a distal end configured to emit a beam of energy. The apparatus also includes a tube including a tube channel. The distal end of the optical fiber is disposed in the tube channel. The apparatus further includes a shock absorber disposed on the tube and a cap disposed on the shock absorber.

15 Claims, 3 Drawing Sheets

(56) References Cited

U.S. PATENT DOCUMENTS

2009/0326525 A1 12/2009 Hixon et al.
2010/0016845 A1 1/2010 Hanley et al.

OTHER PUBLICATIONS

International Search Report and Written Opinion issued in PCT International Application No. PCT/US2011/044951, mailed Feb. 3, 2012.

Boston Scientific Corporation, "DuoTome SideLite Fiber: for Holmium Laser Ablation of the Prostate," 2007, 2 pages.

Fiber Options, Inc., "Learning About Options in Fiber," Oct. 1994, 53 pages.

Kouzmina, Inna, "Better Coating Through Chemistry: Research in Optical Fiber Coatings," Spring 2004, vol. 6e, 4 pages.

* cited by examiner

LASER ASSEMBLY WITH SHOCK ABSORBER

This application claims the benefit of priority from U.S. Provisional Application No. 61/368,130, filed Jul. 27, 2010, which is herein incorporated by reference in its entirety.

FIELD OF THE INVENTION

Embodiments of the invention include medical devices and more particularly medical devices including a laser assembly with a shock absorber and related methods of use.

BACKGROUND OF THE INVENTION

Laser assemblies, including side fire laser assemblies, may be used for laser-based surgical procedures, for example, to deliver laser energy of a specific wavelength at a specific pulse rate to remove tissue through vaporization. Such procedures may be performed in an aqueous environment, for example, within water.

FIG. 1 shows a conventional side fire laser assembly 100 including a side fire optical fiber 130. An end 132 of the optical fiber 130 may be polished at a specific angle such that energy is emitted to a side of the optical fiber 130, as opposed to the end. To permit the laser to emit energy at the correct angle, an air interface is provided at the polished end 132 of the optical fiber 130. As shown in FIG. 1, an air gap 160 is formed in the conventional laser assembly 100 when a capillary tube 150 is fused to the optical fiber 130 and an end 152 of the capillary tube 150 is heated until the end of the capillary tube 150 collapses, thereby forming the air gap 160. A metal cap 170 may be placed over the end 152 of the capillary tube 150. Adhesive 180 may be used to adhere the metal cap 170 to the capillary tube 150 and to adhere the capillary tube 150 and the metal cap 170 to an outer layer 138 of the optical fiber 130. The metal cap 170 helps to protect and reinforce the capillary tube 150 during energy delivery through the laser assembly 100.

During a procedure, such as Holmium laser ablation of the prostate (HoLAP), this conventional laser assembly 100 may be used to deliver laser energy to ablate prostatic tissue for the purpose of alleviating symptoms of Benign Prostatic Hyperplasia (BPH). BPH is a common condition in which the prostate becomes enlarged with aging, which can squeeze the urethra and cause irritation or obstruction of urine flow. Laser-based surgical procedures employing side-firing optical fibers and high-power lasers may be used to remove obstructing prostate tissue, e.g., associated with BPH. The conventional laser assembly 100 may include a laser (not shown), such as a Holmium:YAG (Ho:YAG) laser, that may generate the laser energy delivered through the optical fiber 130. Holmium laser treatment is a minimally invasive alternative to transurethral resection of the prostate (TURP).

The conventional laser assembly can operate at 100 W of average power. This means that, for every second, 100 J (joules) of energy can pass through the optical fiber. The laser assembly can operate in a pulse mode with a pulse rate of 50 Hz and a pulse duration of 200 µs (microseconds). Each pulse therefore can deliver 2 J (100 J/50 Hz) and 10,000 W of power ($2 J/200 \mu s = 2 J/0.2 \times 10^{-3} s = 10 \times 10^3 W$). This pulsed Holmium energy may react with the water surrounding the laser assembly 100 and may create vapor bubbles upon exiting the optical fiber 130 and the capillary tube 150. These vapor bubbles may collapse back violently, which may subject the optical fiber 130 and the capillary tube 150 to significant forces. At a high pulse rate (e.g., 50 Hz), these forces may cause the optical fiber 130 to vibrate, which may in turn break down the brittle adhesive 180 holding the metal cap 170 onto the capillary tube 150. Over time, the adhesive 180 may break loose, may burn up due to the heat generated during energy delivery, and/or may fall out of the metal cap 170. As a result, a substantial gap may be formed between the metal cap 170 and the capillary tube 150 due to the absence of the adhesive 180. The gap between the capillary tube 150 and the metal cap 170 may cause the capillary tube 150 to vibrate against the rigid surfaces of the metal cap 170 as the laser assembly 100 continues delivering the pulses of laser energy. The vibrations of the capillary tube 150 against the metal cap 170 may cause the capillary tube 150 to fracture and may cause pieces of the capillary tube 150 to break away. As a result, the capillary tube 150 is rendered unusable and must be replaced. Accordingly, a need exists for a laser assembly that can withstand high vibrations.

It is to be understood that both the foregoing general description and the following detailed description are exemplary and explanatory only and are not restrictive of the invention.

SUMMARY OF THE INVENTION

In accordance with an embodiment, an apparatus includes an optical fiber having a distal end configured to emit a beam of energy. The apparatus also includes a tube including a tube channel. The distal end of the optical fiber is disposed in the tube channel. The apparatus further includes a shock absorber disposed on the tube and a cap disposed on the shock absorber.

In accordance with another embodiment, a method of forming an apparatus includes disposing a distal end of an optical fiber within a channel in a tube. The optical fiber is configured to emit energy. The method also includes disposing at least a portion of the tube in a shock absorber and disposing the shock absorber in a cap.

In accordance with a further embodiment, an apparatus includes an optical fiber having a distal end configured to emit a beam of energy at an angle relative to a longitudinal axis of the optical fiber. The apparatus also includes a first tube including a tube channel. The distal end of the optical fiber is disposed in the tube channel. The apparatus further includes a second tube. At least a portion of the first tube is disposed in the second tube. The apparatus also includes a cap. At least a portion of the second tube is disposed in the cap.

Additional objects and advantages of the invention will be set forth in part in the description which follows, and in part will be obvious from the description, or may be learned by practice of the invention. The objects and advantages of the invention will be realized and attained by means of the elements and combinations particularly pointed out below.

It is to be understood that both the foregoing general description and the following detailed description are exemplary and explanatory only and are not restrictive of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DESCRIPTION OF THE EMBODIMENTS

Reference will now be made in detail to exemplary embodiments of the invention, examples of which are illustrated in the accompanying drawings. Wherever possible, the same reference numbers will be used throughout the drawings to refer to the same or like parts.

The terms "proximal" and "distal" are used herein to refer to the relative positions of the components of an exemplary laser assembly 10. When used herein, "proximal" refers to a position relatively closer to the exterior of the body, or closer to the surgeon or other user using the laser assembly 10. In contrast, "distal" refers to a position relatively further away from the surgeon or other user using the laser assembly 10, or closer to the interior of the body.

The devices and methods described herein are generally related to the use of optical fibers within the body of a patient, including side fire optical fibers. For example, the devices and methods may be suitable for use in treating symptoms related to an enlarged prostate gland, such as BPH. In these procedures, a doctor may pass the optical fiber through the urethra using a cystoscope, a specialized endoscope with a small camera on the end, and then may deliver multiple pulses of laser energy to destroy some of the enlarged prostate tissue and to shrink the size of the prostate. The devices and methods described herein may be used to treat conditions of the body other than BPH, such as, for example, fibroids, bladder stones, female stress incontinence (FSI), gastro-esophagus reflux diseases (GERD), and/or tumors (e.g., breast cancer tumors).

Figure 1:
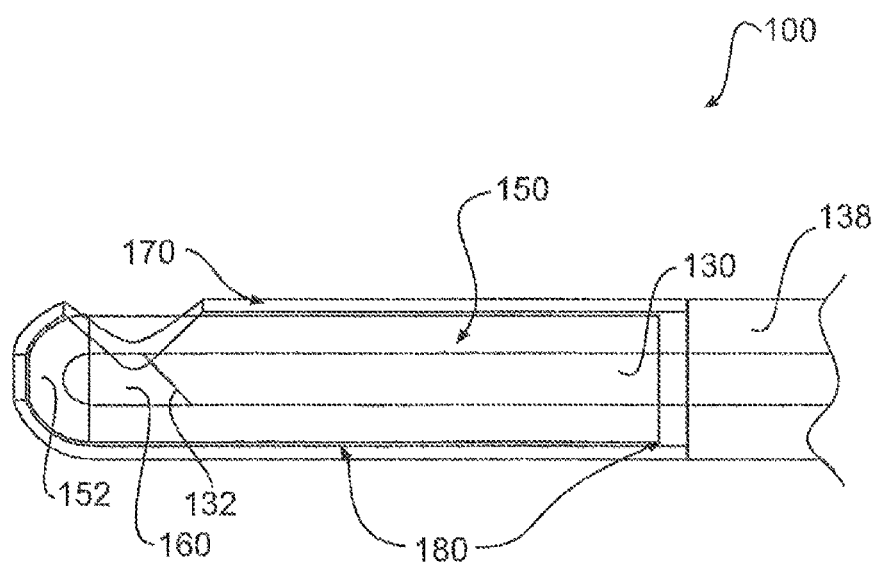
FIG. 1 is a cross-sectional view of a distal end portion of a conventional laser assembly.
Figure 2:
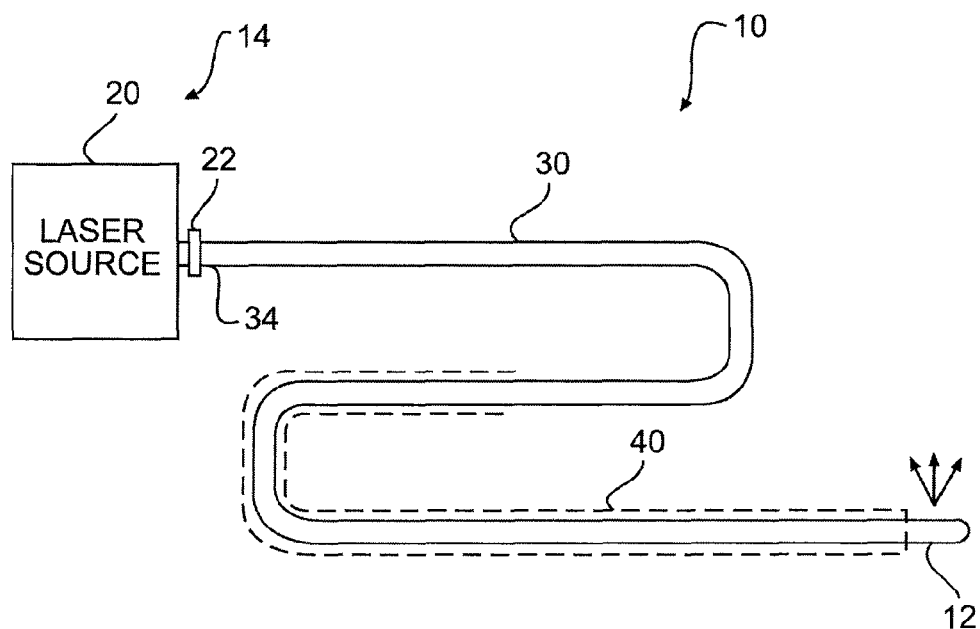
FIG. 2 is a schematic view of a laser assembly, according to an exemplary embodiment of the invention.

FIG. 2 is a schematic drawing of the side fire laser assembly 10 according to an exemplary embodiment. The laser assembly 10 may include a distal end portion 12 and a proximal end portion 14. The laser assembly 10 may also include a laser source 20 and an optical fiber 30. The laser source 20 may be located in the proximal end portion 14 of the laser assembly 10, and the optical fiber 30 may extend between and into the proximal and distal end portions 12, 14 of the laser assembly 10. The laser assembly 10 may be used to transmit laser energy from the laser source 20 to a target treatment area within a patient's body, e.g., near the distal end portion 12 of the laser assembly 10.

The laser source 20 may include at least one laser that may be used to generate laser energy for surgical procedures. The laser source 20 may include at least one of, for example, a Ho:YAG laser, a neodymium-doped:YAG (Nd:YAG) laser, a semiconductor laser diode, or a potassium-titanyl phosphate crystal (KTP) laser. The laser source 20 may include more than one laser, and more than one laser may be used during a surgical procedure. The laser source 20 may also include a processor that provides timing, wavelength, and/or power control of the laser(s). For example, the laser source 20 may include one or more mechanisms for laser selection, filtering, temperature compensation, and/or Q-switching operations.

The optical fiber 30 may include a distal end 32 (FIGS. 3-5) and a proximal end 34. The proximal end 34 of the optical fiber 30 may be coupled to the laser source 20 in the proximal end portion 14 of the laser assembly 10. For example, the proximal end 34 of the optical fiber 30 may be coupled to the laser source 20 through an optical coupler 22 in or near the proximal end portion 14 of the laser assembly 10. The optical coupler 22 may be, for example, an SMA (SubMiniature version A) connector. The proximal end 34 of the optical fiber 30 may be configured to receive laser energy from the laser source 20 via the optical coupler 22, and the optical fiber 30 may be configured to output the laser energy through the distal end 32 of the optical fiber 30. The optical fiber 30 may include, for example, a core, one or more cladding layers about the core, a buffer layer about the cladding, a jacket, etc. The core may be made of a suitable material for the transmission of laser energy from the laser source 20. The core may be multi-mode and may have a step or graded index profile. The cladding may be a single or a double cladding that may be made of a hard polymer or silica. The buffer may be made of a hard polymer such as Tefzel®, for example. When the optical fiber 30 includes a jacket, the jacket may be made of Tefzel®, for example, or other polymers. The optical fiber 30 may be made of a suitable biocompatible material and may be flexible, for example, to traverse tortuous anatomy in the body.

The laser assembly 10 may also include a suitable catheter or endoscope 40 for inserting the distal end portion 12 of the laser assembly 10 into a patient's body. The endoscope 40 may define one or more lumens. In some embodiments, the endoscope 40 may include a single lumen that may receive various components such as the optical fiber 30. The endoscope 40 may have a proximal end configured to receive the distal end 32 of the optical fiber 30 and a distal end configured to be inserted into a patient's body for positioning the distal end 32 of the optical fiber 30 in an appropriate location for a laser-based surgical procedure. For example, to perform a surgical procedure near the prostate, the endoscope 40 may be used to place the distal end 32 of the optical fiber 30 at or near the prostate gland. The endoscope 40 may be made of a suitable biocompatible material and may include an elongate portion that may be flexible to allow the elongate portion to be maneuvered within the body. The endoscope 40 may also be configured to receive various other medical devices or tools through one or more lumens of the endoscope 40, such as, for example, irrigation and/or suction devices, forceps, drills, snares, needles, etc. In some embodiments, the endoscope 40 may include a fluid channel (not shown) coupled at a proximal end to a fluid source (not shown). The fluid channel may be used to irrigate an interior of the patient's body during a laser-based surgical procedure. In some embodiments, the endoscope 40 may include an optical device (not shown), e.g., including an eyepiece coupled to a proximal end of the endoscope 40. The optical device may include an optical fiber or other image transmission device, e.g., a wireless device, that may be disposed in or on the endoscope 40, e.g., in a lumen or on a distal end of the endoscope 40, to transmit an image signal to the surgeon. Such an embodiment allows a medical practitioner to view the interior of a patient's body through the eyepiece.

Figure 3:
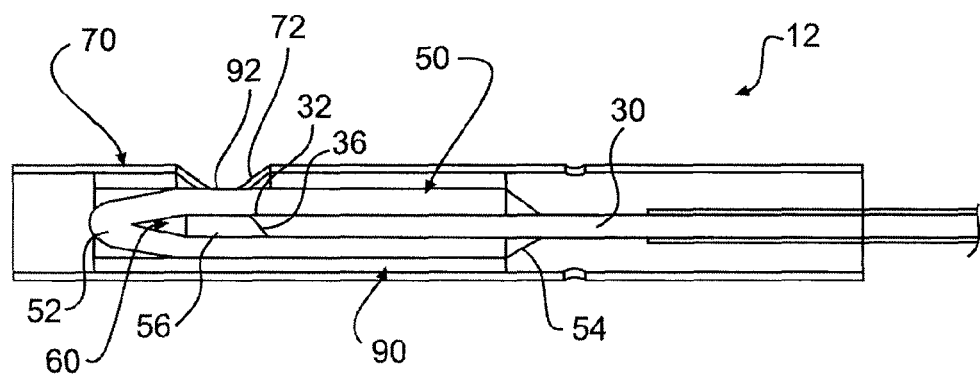
FIG. 3 is a cross-sectional view of the distal end portion of the laser assembly of FIG. 2, according to an exemplary embodiment of the invention.
Figure 4:
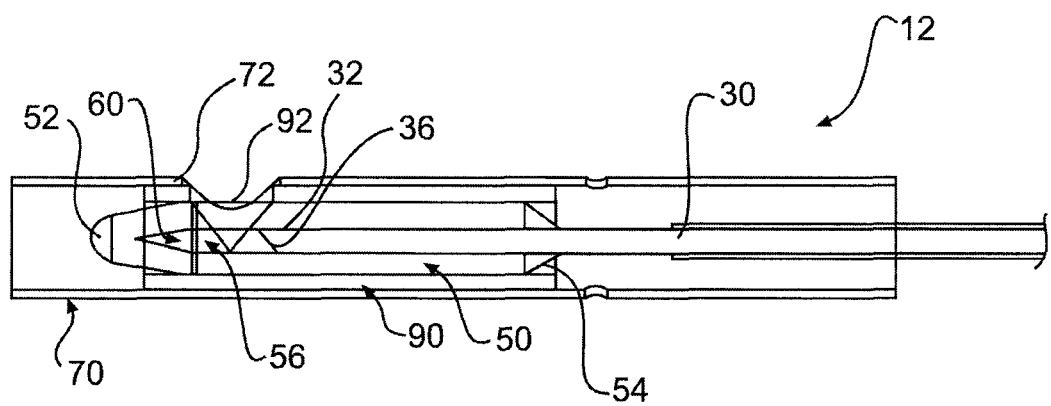
FIG. 4 is a cross-sectional view of the distal end portion of the laser assembly of FIG. 2, according to another exemplary embodiment of the invention.
Figure 5:
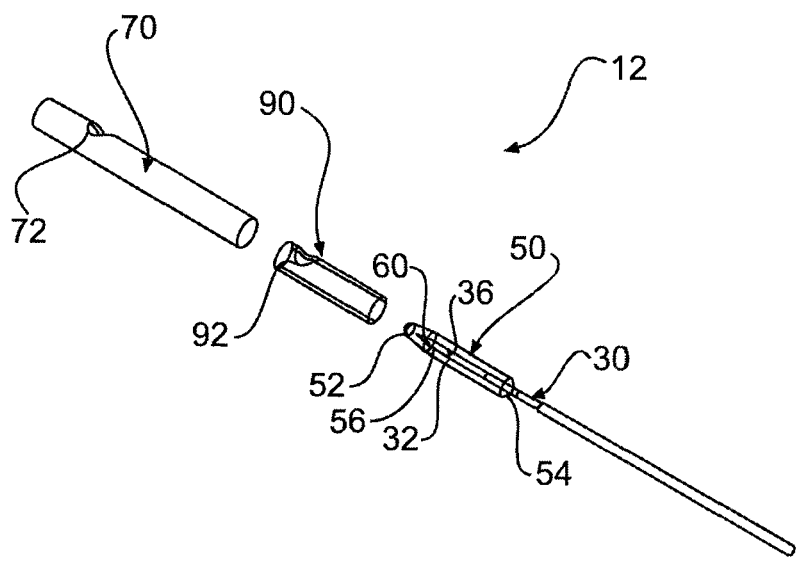
FIG. 5 is an exploded view of the distal end portion of the laser assembly of FIG. 4.

FIG. 3 shows the distal end portion 12 of the laser assembly 10, according to an exemplary embodiment. FIG. 4 shows the distal end portion 12 of the laser assembly 10, according to another exemplary embodiment. FIG. 5 is an exploded view of the distal end portion 12 of the laser assembly 10 of FIG. 4. The embodiments of FIGS. 3-5 generally differ in the positioning and/or size of the components of the distal end portion 12 of the laser assembly 10 as described below. As noted above, the same reference numbers have been used in FIGS. 3-5 to refer to the same or like parts.

The distal end 32 of the optical fiber 30 may form an angled portion 36 in the distal end portion 12 of the laser assembly 10. The angled portion 36 has an angled surface at the distal end 32 of the optical fiber 30. The angled surface is transverse to a plane that is perpendicular to a longitudinal axis of the optical fiber 30. The distal end portion 12 of the laser assembly 10 (including the angled portion 36) may be inserted into the patient's body to provide laser treatment. An optical beam (e.g., laser beam including laser energy) may be transmitted from the laser source 20, through the optical fiber 30 from its proximal end 34 to its distal end 32, and then through the angled portion 36 at the distal end 32 of the optical fiber 30. The angled portion 36 may be cleaved and/or polished to an appropriate angle configured to redirect laser energy in a lateral direction for side-firing transmission of laser energy to the area of treatment in the patient's body. Thus, the distal end 32 of the optical fiber 30 may include one or more members, elements, components, configurations, or shapes that may individually or collectively operate to transmit laser energy in generally a lateral direction offset from a longitudinal axis or centerline of the distal end 32 of the optical fiber 30.

The distal end 32 of the optical fiber 30 may be disposed within a channel 56 in a capillary tube 50 in the distal end portion 12 of the laser assembly 10. The capillary tube 50 may include a distal end 52 and a proximal end 54, and the channel 56 may extend longitudinally between the distal and proximal ends 52, 54. The capillary tube 50 may be made of, for example, at least one of silica, sapphire, glass, calcium fluoride, Cleartran™, multispectral zinc sulphide (MS ZnS), fused silica, gallium arsenide, gallium phosphide, plastic, Pyrex®, SF57, high index glass, silicon, zinc selenide, zinc sulfide, and/or other like materials. The proximal end 54 of the capillary tube 50 may be formed at an angle to have a frustoconical shape, as shown in FIGS. 3-5, or flat.

An outer surface of the distal end 32 of the optical fiber 30 may be positioned flush against an inner surface of the capillary tube 50, as shown in FIGS. 3-5, and may be attached to the inner surface of the capillary tube 50. For example, the outer surface of the distal end 32 of the optical fiber 30 may be fused to the inner surface of the capillary tube 50. Fusing may reduce or eliminate any air gap between the inner surface of the capillary tube 50 and the outer surface of the optical fiber 30, which may reduce or eliminate losses in energy that may occur when passing energy through such an air gap. Alternatively, the outer surface of the distal end 32 of the optical fiber 30 may be attached to the inner surface of the capillary tube 50 without fusing the optical fiber 30 and the capillary tube 50 together. The attachment may be provided near the distal end 32 of the optical fiber 30, near a proximal end 54 of the capillary tube 50, and/or at a location between the optical fiber distal end 32 and the capillary tube proximal end 54. For example, the optical fiber 30 and the capillary tube 50 may be attached using compression, glue, or by using another type of structure or method for fastening or holding the optical fiber 30 and the capillary tube 50 together.

The optical fiber 30 may be disposed through a proximal part of the channel 56 in the capillary tube 50, and the distal end 52 of the capillary tube 50 may be closed, as shown in FIGS. 3-5, e.g., by heating (to soften) and/or collapsing the distal end 52. The distal end 52 of the capillary tube 50 may also be formed at an angle to have a conical shape, as shown in FIGS. 3-5, a frustoconical shape, flat, etc. The distal end 32 of the optical fiber 30 may be inserted into the proximal end 54 of the capillary tube 50 such that the channel 56 remains at least partially empty (except for air) and the distal end 52 of the capillary tube 50 may be distal to the angled portion 36 of the optical fiber 30. Since the channel 56 is at least partially empty, a gap 60 or air pocket is formed in the channel 56 at a location that is distal from the distal end 32 of the optical fiber 30.

As shown in FIGS. 3 and 4, a cap 70 may be inserted over the capillary tube 50 in the distal end portion 12 of the laser assembly 10. Thus, the cap 70 is a distal casing for the capillary tube 50 that encloses the capillary tube 50 and the distal end 32 of the optical fiber 30. The cap 70 may be formed, for example, of a biocompatible and/or thermally conductive material, such as a metal, metal alloy, and/or other rigid material. The cap 70 helps to protect and reinforce the capillary tube 150 during energy delivery through the laser assembly 10.

As shown in FIGS. 3 and 4, a shock absorber/dampening element 90 may be disposed between the capillary tube 50 and the cap 70 in the distal end portion 12 of the laser assembly 10. The shock absorber 90 may extend along substantially the entire length of the capillary tube 50. For example, as shown in FIG. 3, the shock absorber 90 may extend generally to the distal end 52 of the capillary tube 50, and the frustoconical tip at the proximal end 54 of the capillary tube 50 may extend outward and proximal from the proximal end of the shock absorber 90. Alternatively, as shown in FIG. 4, the conical tip at the distal end 52 of the capillary tube 50 may extend outward and distal from the distal end of the shock absorber 90. Also, the shock absorber 90 may extend generally to the proximal end 54 of the capillary tube 50. The shock absorber 90, as a further example, may extend from a position distal to the distal end 52 to a position proximal to the proximal end 54, so as to completely surround the capillary tube 50. The shock absorber 90 may extend along (e.g., parallel to or coaxial with) the surface of the capillary tube 50 that is parallel to or coaxial with the inner surface of the cap 70. Thus, the shock absorber 90 may extend along the surface of the capillary tube 50 that is closest to the inner surface of the cap 70 and may prevent the capillary tube 50 from directly contacting the inner surface of the cap 70.

As shown in FIGS. 3-5, the shock absorber 90 may include an opening 92 or window, and the cap 70 may include an opening 72 or window. The openings 72, 92 are aligned. The openings 72, 92 may be laser cut or otherwise formed in the respective shock absorber 90 or cap 70 to allow the energy to be delivered from the angled portion 36 of the optical fiber 30 through the shock absorber 90 and the cap 70.

The shock absorber 90 may be formed of one or more layers of material. The shock absorber 90 may be formed of a flexible material and/or a rigid material, such as, but not limited to silicone, fluorinated ethylene propylene (FEP), polytetrafluoroethylene (PTFE), polycarbonate (PC), acrylonitrile butadiene styrene (ABS), nylon, polypropylene, polyethylene, thermoplastic elastomer (TPE), thermoplastic rubber (TPR), polyvinyl chloride (PVC), acrylate polymer, other rubbery and/or soft materials, other polymers, etc. The shock absorber 90 may be formed of a material that is less brittle than the material of the capillary tube 50. Also, the shock absorber 90 may be formed of a material that is softer, more flexible or elastic, and/or less rigid or stiff than the material of the capillary tube 50 and/or the cap 70. In an embodiment, the shock absorber 90 may be a stiff, thermally-resistant coating or layer that may have a higher heat tolerance and resistance to abrasion from general handling.

The shock absorber 90 may be formed using various methods, such as methods used for forming generally tubular members, e.g., extrusion or molding. Alternatively, the shock absorber 90 may be formed as a flat or sheet member, which may be wrapped around the capillary tube 50, inserted against the inner surface of the cap 70, or inserted between the capillary tube 50 and the cap 70.

The shock absorber 90 may be formed from a liquid or gel, e.g., flexible or rigid adhesives, injectable silicone, etc. For example, a liquid or gel for forming the shock absorber 90 may be dispensed over the capillary tube 50 before the capillary tube 50 is inserted into the cap 70. Alternatively, the liquid or gel may be dispensed onto the inner surface of the cap 70 before the capillary tube 50 is inserted into the cap 70. As another alternative, the liquid or gel may be dispensed between the capillary tube 50 and the cap 70 after the capillary tube 50 is disposed inside the cap 70. The liquid or gel may remain in the liquid or gel state to serve as the shock absorber 90, or may be partially or entirely solidified.

The shock absorber 90 may be formed from a heatshrink material. The heatshrink material in the unheated state may be in the form of a tube that is placed over the capillary tube 50, e.g., before or after the capillary tube 50 is inserted into the cap 70, and then heated so that the heatshrink material shrinks around the capillary tube 50. In this embodiment, no space exists between the capillary tube 50 and the shock absorber 90. In other embodiments, such as shown in FIGS. 3 and 4, spaces may exist between the capillary tube 50 and the shock absorber 90.

The capillary tube 50, the shock absorber 90, and the cap 70 may be assembled together using various methods. For example, the shock absorber 90 may be formed separately from the capillary tube 50 and the cap 70 (i.e., before contacting the capillary tube 50 or the cap 70), for example, by extrusion or molding. For example, the shock absorber 90 may be formed over a carrier (not shown), e.g., by molding the shock absorber 90 over the carrier, and then the shock absorber 90 may be removed from the carrier. Alternatively, the shock absorber 90 may be extruded or otherwise formed without using a carrier.

After separately forming the shock absorber 90, the shock absorber 90 may be assembled with the capillary tube 50 and the cap 70. For example, the capillary tube 50 may be inserted into the separately-formed shock absorber 90, and then the shock absorber 90 and capillary tube 50 may be inserted together into the cap 70. Alternatively, the separately-formed shock absorber 90 may be inserted into the cap 70, and then the capillary tube 50 may be inserted into the shock absorber 90. As another alternative, the capillary tube 50 may be inserted into the cap 70, and then the separately-formed shock absorber 90 may be inserted between the capillary tube 50 and the cap 70.

Instead of separately forming the shock absorber 90, the shock absorber 90 may be formed or applied directly onto the capillary tube 50, e.g., by molding, coating, or laminating the shock absorber 90 onto the capillary tube 50. Alternatively, the shock absorber 90 may be formed or applied directly inside the cap 70, e.g., by being molded, coated, or laminated inside the cap 70, before inserting the capillary tube 50 into the shock absorber 90.

The cap 70 may be sized appropriately to receive the different components, e.g., the shock absorber 90, the capillary tube 50, and the distal end 32 of the optical fiber 30. The cap 70 may be attached to the outer surface of the shock absorber 90, the shock absorber 90 may be attached to the outer surface of the capillary tube 50, and the capillary tube 50 may be attached to the outer surface of the optical fiber 30 using, for example, an adhesive or glue, by compression or friction fit, etc., or any other methods described above. The cap 70 may have a length extending over both a proximal end and a distal end of the shock absorber 90, as shown in FIGS. 3-5.

The shock absorber 90 may serve as a cushioning barrier between the capillary tube 50 and the cap 70. As noted above, each laser pulse from the laser source 20 is capable of generating very intense vibrations, and the vibrations may cause the capillary tube 150 of the conventional laser assembly 100 to break or fracture. The shock absorber 90 according to the exemplary embodiments may serve to reduce the amount of vibrations in the distal end portion 12 of the laser assembly 10 by cushioning the capillary tube 50. The shock absorber 90 may dampen or absorb the shocks, vibrations, or other forces acting on the capillary tube 50 due to the laser pulses. As a result, the capillary tube 50 may be prevented from contacting or vibrating against the cap 70. By reducing these vibrations, the shock absorber 90 may prevent breakage or fracture of the capillary tube 50.

Any aspect set forth in any embodiment may be used with any other embodiment set forth herein. Every device and apparatus set forth herein may be used in any suitable medical procedure, may be advanced through any suitable body lumen and body cavity, and may be used for treatment of any suitable body portion. For example, the apparatuses and methods described herein may be used in any natural body lumen or tract, including those accessed orally, vaginally, or rectally.

It will be apparent to those skilled in the art that various modifications and variations can be made in the disclosed systems and processes without departing from the scope of the invention. Other embodiments of the invention will be apparent to those skilled in the art from consideration of the specification and practice of the invention disclosed herein. It is intended that the specification and examples be considered as exemplary only. The following disclosure identifies some other exemplary embodiments.

In some embodiments, an apparatus may include an optical fiber having a distal end configured to emit a beam of energy. The apparatus may also include a tube including a tube channel. The distal end of the optical fiber may be disposed in the tube channel. The apparatus may further include a shock absorber disposed on the tube and a cap disposed on the shock absorber.

In some embodiments, an inner surface of the shock absorber may contact an outer surface of the tube, and an outer surface of the shock absorber may contact an inner surface of the cap.

In some embodiments, the shock absorber may be formed of a less brittle material than the tube and a less stiff material than the cap.

In some embodiments, the shock absorber may extend over substantially the entire outer surface of the tube and may include an opening in a surface extending generally parallel to a longitudinal axis of the optical fiber. The opening may be located generally laterally from the distal end of the optical fiber.

In some embodiments, the shock absorber may be configured to be disposed on the tube before being disposed in the cap or disposed in the cap before being disposed on the tube.

In some embodiments, the shock absorber may be formed from a material inserted between the tube and the cap.

In some embodiments, the shock absorber may be formed from a liquid or gel.

In some embodiments, the shock absorber may include a heatshrink material.

In some embodiments, at least a portion of the cap may be metal.

In some embodiments, the shock absorber may be formed of at least one of silicone, fluorinated ethylene propylene, polytetrafluoroethylene, polycarbonate, acrylonitrile butadiene styrene, nylon, polypropylene, polyethylene, thermoplastic elastomer, thermoplastic rubber, or polyvinyl chloride.

In some embodiments, the apparatus may further include a laser source coupled to the optical fiber and configured to produce the beam of energy.

In some embodiments, the distal end of the optical fiber may be configured to emit the beam of energy at an angle relative to a longitudinal axis of the optical fiber.

In some embodiments, a distal surface of the distal end of the optical fiber may include an angled surface configured to direct at least a portion of the beam of energy laterally from the optical fiber.

In some embodiments, a method of forming an apparatus may include disposing a distal end of an optical fiber within a channel in a tube. The optical fiber may be configured to emit energy. The method may also include disposing at least a portion of the tube in a shock absorber and disposing the shock absorber in a cap.

In some embodiments, the method may further include disposing the shock absorber on the tube before disposing the shock absorber in the cap, or disposing the shock absorber in the cap before disposing the shock absorber on the tube.

In some embodiments, the method may further include inserting a material for forming the shock absorber between the tube and the cap.

In some embodiments, the optical fiber may include a distal surface configured to emit energy at an angle relative to a longitudinal axis of the optical fiber.

In some embodiments, an apparatus may include an optical fiber having a distal end configured to emit a beam of energy at an angle relative to a longitudinal axis of the optical fiber. The apparatus may also include a first tube including a tube channel. The distal end of the optical fiber may be disposed in the tube channel. The apparatus may further include a second tube. At least a portion of the first tube may be disposed in the second tube. The apparatus may also include a cap. At least a portion of the second tube may be disposed in the cap.

In some embodiments, an inner surface of the second tube may contact an outer surface of the first tube, and an outer surface of the second tube may contact an inner surface of the cap.

In some embodiments, the second tube may extend over substantially the entire outer surface of the first tube and may include an opening in a surface extending generally parallel to the longitudinal axis of the optical fiber. The opening may be located generally laterally from the distal end of the optical fiber.

What is claimed is:

1. An apparatus comprising:
    an optical fiber having a distal end configured to emit a beam of energy wherein a distal surface of the distal end of the optical fiber includes an angled surface configured to direct at least a portion of the beam of energy laterally from the optical fiber;
    a tube including a tube channel, the distal end of the optical fiber being disposed in the tube channel;
    a shock absorber disposed on a portion of the tube and extending distally beyond the distal tip of the optical fiber, wherein the shock absorber is heatshrink coupled to the tube; and
    a cap disposed on the shock absorber.

2. The apparatus of claim 1, wherein a portion of an inner surface of the shock absorber contacts a portion of an outer surface of the tube, and an outer surface of the shock absorber contacts an inner surface of the cap.

3. The apparatus of claim 1, wherein the shock absorber is formed of a less brittle material than the tube and a less stiff material than the cap.

4. The apparatus of claim 1, wherein the shock absorber includes an opening in a surface extending generally parallel to a longitudinal axis of the optical fiber, the opening located generally laterally from the distal end of the optical fiber.

5. The apparatus of claim 1, wherein the shock absorber is configured to be disposed on the portion of the tube before being disposed in the cap or disposed in the cap before being disposed on the portion of the tube.

6. The apparatus of claim 1, wherein the shock absorber is formed from a material inserted between the tube and the cap.

7. The apparatus of claim 1, wherein at least a portion of the cap is metal.

8. The apparatus of claim 1, wherein the shock absorber is formed of at least one of silicone, fluorinated ethylene propylene, polytetrafluoroethylene, polycarbonate, acrylonitrile butadiene styrene, nylon, polypropylene, polyethylene, thermoplastic elastomer, thermoplastic rubber, or polyvinyl chloride.

9. The apparatus of claim 1, further including a laser source coupled to the optical fiber and configured to produce the beam of energy.

10. A method of forming an apparatus, the method comprising:
    disposing a distal end of an optical fiber within a channel in a tube, the optical fiber being configured to emit energy and the tube being configured to pass emitted energy laterally therethrough;
    disposing a portion of the tube in a shock absorber;
    heatshrink coupling the shock absorber to the tube; and
    disposing the shock absorber in a cap, the shock absorber being less stiff than the cap.

11. The method of claim 10, further including disposing the shock absorber on the portion of the tube before disposing the shock absorber in the cap, or disposing the shock absorber in the cap before disposing the shock absorber on the portion of the tube.

12. The method of claim 10, further including inserting a material for forming the shock absorber between the tube and the cap.

13. The method of claim 10, wherein the optical fiber includes a distal surface configured to emit energy at an angle relative to a longitudinal axis of the optical fiber.

14. An apparatus comprising:
    an optical fiber having a distal end configured to emit a beam of energy at an angle relative to a longitudinal axis of the optical fiber;
    a first tube including a tube channel, the distal end of the optical fiber being disposed in the tube channel,
    a shock absorber, a portion of the first tube being disposed in the shock absorber; and
    a cap, at least a portion of the shock absorber being disposed in the cap, wherein the shock absorber is less brittle than the first tube and less stiff than the cap;
    wherein the shock absorber includes an opening in a surface extending generally parallel to the longitudinal axis of the optical fiber, the opening located generally laterally from the distal end of the optical fiber.

15. The apparatus of claim 14, wherein a portion of an inner surface of the shock absorber contacts a portion of an outer surface of the first tube.

* * * * *